United States Patent [19]

Koch, III et al.

[11] Patent Number: 5,533,510
[45] Date of Patent: Jul. 9, 1996

[54] REAL TIME ULTRASOUND ENDOCARDIAL DISPLACEMENT DISPLAY

[75] Inventors: Albert F. Koch, III, Newburyport; David M. Prater, Melrose, both of Mass.

[73] Assignee: Hewlett-Packard Company, Palo Alto, Calif.

[21] Appl. No.: 532,264

[22] Filed: Sep. 22, 1995

Related U.S. Application Data

[63] Continuation of Ser. No. 308,718, Sep. 19, 1994, abandoned, which is a continuation-in-part of Ser. No. 275,554, Jul. 15, 1994, abandoned.

[51] Int. Cl.$^6$ .................................................. H61B 8/00
[52] U.S. Cl. .................................................. 128/660.07
[58] Field of Search .......... 128/660.01, 660.04–660.05, 128/660.07, 661.01, 661.08, 661.09, 653.1–653.4; 73/626; 364/413.25; 382/130

[56] References Cited

U.S. PATENT DOCUMENTS

| | | | |
|---|---|---|---|
| 5,040,225 | 8/1991 | Gouge | 382/6 |
| 5,148,809 | 9/1992 | Biegeleisen-Knight et al. | 128/660.07 |
| 5,151,856 | 9/1992 | Halmann et al. | 364/413.03 |
| 5,156,152 | 10/1992 | Yamazaki et al. | 128/660.04 |
| 5,195,521 | 3/1993 | Melton, Jr. et al. | 128/660.02 |
| 5,224,481 | 7/1993 | Ishihara et al. | 128/660.07 |
| 5,233,993 | 8/1993 | Kawano | 128/660.07 |
| 5,241,473 | 8/1993 | Ishihara et al. | 128/660.01 |
| 5,257,624 | 11/1993 | Fraser et al | 128/660.01 |
| 5,279,302 | 1/1994 | Tamano et al. | 128/661.09 |
| 5,285,788 | 2/1994 | Arenson et al. | 128/660.05 |
| 5,322,067 | 6/1994 | Prater et al. | 128/660.07 |
| 5,355,887 | 10/1994 | Iizuka et al. | 128/660.04 |

FOREIGN PATENT DOCUMENTS

0585070A1  8/1993  European Pat. Off. .

*Primary Examiner*—Francis Jaworski

[57] ABSTRACT

An ultrasound display apparatus provides a two-dimensional display of a fluid filled cavity and surrounding wall tissue in the form of a sequence of pixel image frames that are shown on a display screen. The apparatus includes circuitry for indicating wall tissue displacements on the screen on a frame by frame basis. The apparatus includes a pixel classification circuit for classifying pixels in each pixel image frame into two types, i.e., tissue or fluid. A frame comparator determines which pixels change classification from one to another type as between a pair of succeeding frames. A color assignment circuit assigns to changed-type pixels in a frame, a color value which causes the changed pixels to be readily differentiated by a viewing user. Different color values are used from frame to frame on both ventricular expansion and contraction cycles.

12 Claims, 6 Drawing Sheets

REAL TIME ULTRASOUND ENDOCARDIAL DISPLACEMENT DISPLAY

This is a continuation of application Ser. No. 08/308,718 filed on Sep. 19, 1994 and now abandoned, which is a continuation-in-part of U.S. patent application Ser. No. 08/275,554 filed Jul. 15, 1994 now abandoned. This invention relates to ultrasound cardiac imaging, and more particularly, to a method and apparatus for precisely imaging ventricular wall movement.

BACKGROUND OF THE INVENTION

Ultrasound imaging of various aspects of the heart is a well known diagnostic modality. Various systems have been designed which enable an ultrasound system to determine the volume of the left ventricle of the heart at various times during the cardiac cycle. Such systems require an ability to accurately identify the endocardium/blood boundary. In U.S. Pat. No. 5,195,521 to Melton, Jr. et al, assigned to the same assignee as this application, a majority vote circuit indicates, at each range along an ultrasound-scan line, when a majority of the signals for both a current scan line and two previous scan lines indicate that reflections of the transmitted pulses are from tissue or blood. In this manner, the tissue/blood interface is accurately determined and is less affected by noise.

U.S. Pat. No. 5,257,624 to Fraser et al describes a gain control circuit which enables the gain along one or more scan lines to be kept substantially constant—thereby enabling a more accurate tissue/blood boundary determination. The accuracy enhancement occurs due because the boundary judgement is based upon a discrimination in levels between return pulses, with tissue generally returning a higher level signal than blood. If the gain of return signals from a scan line vary significantly due to tissue attenuation, tissue/blood boundary determination is rendered substantially more complex.

In U.S. Pat. No. 5,322,067 to Prater et al, (assigned to the same assignee as this application) describes an improved technique for determining volumetric efficiency of the left ventricle. An ultrasound display of the left ventricle and surrounding tissue is obtained and the user traces a region of interest around the ventricle at the largest volume for which a volume determination is to be made. Each pixel of the ultrasound image, within the region of interest, is classified as a blood pixel or a tissue pixel. The area of blood pixels within each display frame is determined and the volume of the ventricle is calculated from the area of the fluid pixels within each segment of the region using the method of disks.

In U.S. Pat. No. 5,285,788 to Arenson et al., an ultrasound imaging system displays a B-mode image and superimpose thereon color Doppler information. The color Doppler information is displayed using a color map which indicates different accerations of a coronary myocardium.

The cardiologist is interested in being able to assess left ventricular function. Ventricular (i.e. endocardium) wall motion is an important aspect of the diagnostic information. The physician wishes to know how much each segment of the endocardium moved and when the individual segment moved with respect to other individual segments. The conditions being assessed are: akinesis (no movement), hypokinesis (partial movement), hyperkinesis (over-active movement), diakinesis (abnormal movement), and tardokinesis (delay of movement). In presently available cardiac ultrasound imaging systems, wall motion assessment by the physician may only be performed only on a qualitative (as contrasted to quantitative) basis. Such an assessment is difficult because the physician's eyes must essentially integrate the movement of each piece of the endocardium wall.

SUMMARY OF THE INVENTION

An ultrasound display apparatus provides a two-dimensional display of a fluid filled cavity and surrounding wall tissue in the form of a sequence of pixel image frames that are shown on a display screen. The apparatus includes circuitry for indicating wall tissue displacements on the screen on a frame by frame basis. The apparatus includes a pixel classification circuit for classifying pixels in each pixel image frame into two types, i.e., tissue or fluid. A frame comparator determines which pixels change classification from one to another type as between a pair of succeeding frames. A color assignment circuit assigns to changed-type pixels in a frame, a color value which causes the changed pixels to be readily differentiated by a viewing user. Different color values are used from frame to frame on both ventricular expansion and contraction cycles. In lieu of different color values, other mapping functions can be employed to distinguish incremental wall tissue movements.

DETAILED DESCRIPTION OF THE PREFERRED EMBODIMENT

Coronary artery disease states are often first signalled by irregularities in contraction phases of the left ventricular wall, i.e., wherein one segment of the wall moves before another segment. While a normal heart function is manifest by substantially concurrent ventricular wall movements, certain coronary insufficiencies are signalled by non-concurrent wall movements. This invention provides both a method and apparatus for enabling the physician to precisely image, on a frame by frame basis, movement of the ventricular wall and to further view a sequence of frames illustrating wall movement in such a manner as to be able to distinguish movement of various segments of the ventricular wall. The invention may be performed on a real time basis as data is being accumulated or may be performed on an off-line basis, from data that has ben acquired and stored for later analysis.

To provide a display which enables wall motion to be visualized, each pixel is initially classified as to whether it is a tissue pixel or a blood pixel. Each pixel is further classified as to a time of occurrence, i.e., either during diastole or systole. During succeeding frames of ultrasound imaging, pixel classification changes from tissue-to-blood or blood-to-tissue are indicative of wall segment movement. Pixels which change from blood-to-tissue are assigned a display color which differs from the pixel's display color in a previous frame—to enable the incremental changes to be precisely viewed. Further, each pixel is assigned a value that is indicative of whether it is occurring during a period of systole or diastole (contraction or expansion). Different incremental color values are assigned to changed pixels during systole and diastole so as to be able to distinguish wall movements occurring during those intervals.

Figure 1:
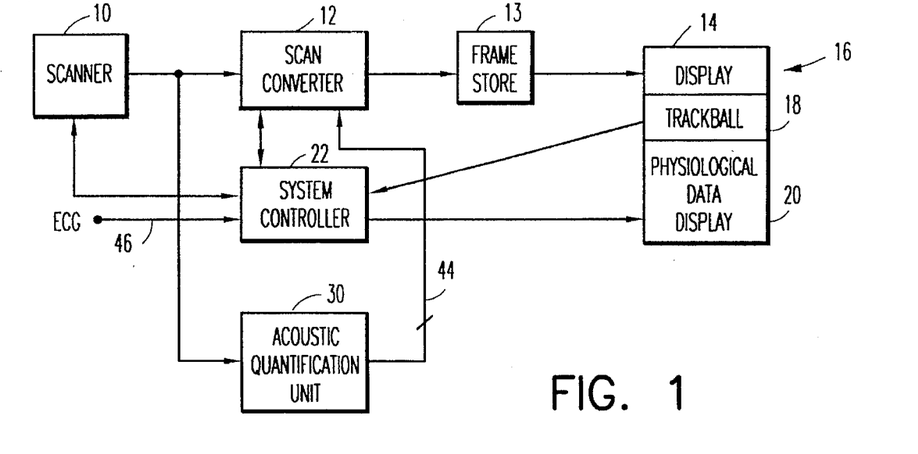
FIG. 1 is a block diagram of an ultrasound imaging system that incorporates the invention hereof.

A simplified diagram of a system that implements the invention is shown in FIG. 1. A scanner 10 performs ultrasound scanning of a specified region of a patient's body, such as the heart. The scanner includes an ultrasound transducer for transmitting and receiving ultrasound energy. The transducer transmits ultrasound energy into a region being imaged and receives reflected ultrasound energy from organs within the patient's body.

As is well known, the transducer may include an array of transducer elements and by appropriately delaying the pulses applied to each transducer element, a focused ultrasound beam is transmitted along a desired scan line. The reflected ultrasound energy from a given point within the patient's body is received by the transducer elements at different times. The transducer elements converge the received ultrasound energy signals, which signals are supplied to a beam former. The beam former processes the return signals and outputs a signal stream that is indicative of a focused, received, beam.

The depth and direction of the focal point of the received beam relative to the ultrasound transducer can be varied dynamically with time by appropriately delaying the received signals from each of the transducer elements. The delayed signals from each transducer element are summed to provide a scanner signal that is a representation of the reflected energy level along a given scan line. The process is repeated for multiple scan lines to provide signals for generating an image of the prescribed region of the patient's body. Typically, the scan pattern is a sector scan wherein the scan lines originate at a point at the center of the ultrasound transducer and are directed at different angles.

Alternatively, scanner 10 can include a mechanical scanner for ultrasound scanning of a specified region of a patient's body. In such a scanner, an ultrasound transducer is scanned across a specified region by a motor (as is well known in the art).

Hereafter, the invention will be discussed in the context of a real-time display system, however, those skilled in the art will realize that the display modality to be hereafter described can be performed off-line on data stored from previous ultrasound scans. The output of scanner 10 is applied to a scan converter 12 which converts the sector scan information generated by scanner 10 to a conventional raster scan display. The output of scan converter 12 is stored in a frame store 13 and is then passed to a display 14 which is part of an operator interface 16. Operator interface 16 may include a track ball 18 for tracing a region of interest to enable further analysis. A physiological data display 20 may also be provided which includes an alphanumeric display of physiologic data and a display of physiological waveforms, such as an ECG trace.

A system controller 22 (i.e., a microprocessor) provides overall control of the ultrasound imaging system. An acoustic quantification unit 30 provides a pixel classification capability and enables each pixel in each frame to be classified as to whether it is blood or tissue and whether the pixel appears during the period of systole or diastole. Acoustic quantification unit may also be employed to determine the volume of a fluid filled cavity. Such an application is described in U.S. Pat. No. 5,322,067 to Prater et al, referred to above. The disclosure of U.S. Pat. No. 5,322,067 is incorporated herein by reference.

Figure 2:
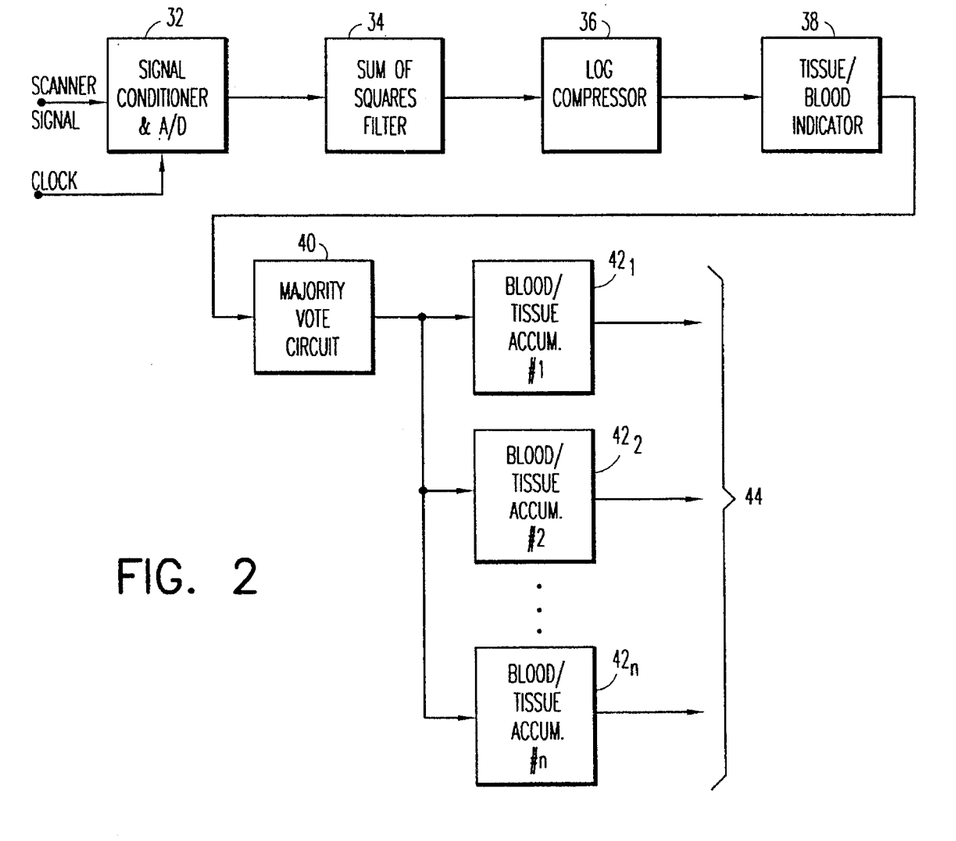
FIG. 2 is a block diagram of an acoustic quantification unit for determining whether a pixel is indicative of a fluid region or a tissue region.

A block diagram of acoustic quantification unit 30 is shown in FIG. 2. A scanner signal from scanner 10 is applied to signal conditioner and analog to digital converter 32 which adjusts the gain of the received scanner signal and converts the analog signal to a series of digital samples. The digital samples are applied to a sum of square filter 34 which squares the signal and integrates the result, using a moving window. The output of filter 34 is supplied to a log compressor 36 which performs a log compression of the form Y=10 LOG X. As the scanner signal contains noise and reflections which may cause an erroneous tissue/blood decision, the accuracy of the decision is increased by averaging along each scan line. That averaging is performed by sum of squares filter 34.

The output of log compressor 36 is applied to a tissue/blood indicator 38 which compares the digital samples with a reference level. The reference level is selected between an amplitude representative of a blood return and a tissue return amplitude. The output of tissue/blood indicator 38 has a first state when the input signal is representative of blood and a second state when the input signal is representative of tissue. The tissue/blood analysis is applied to each digitized sample input. Thus, for each digitized return sample, a tissue/blood determination is rendered so as to enable a differentiation, frame-to-frame, as to whether a pixel location has changed from blood-to-tissue or vice-versa.

The accuracy of the blood/tissue decision is increased by applying the output of tissue/blood indicator 38 to a majority vote circuit 40. Majority votes circuit 40 performs an effective averaging by comparing decisions for each digitized signal sample with decisions for digitized signal samples at the same depth on adjacent scan lines of the ultrasound image. The result of the majority vote circuit is determined by state of a majority of the samples considered.

The majority vote process is preferably performed for a group of samples at the same depth on several successive scan lines, typically three, to provide higher accuracy. The number of samples used to perform the majority vote can be varied, depending upon circumstances. Majority vote circuit 40 outputs a signal that is active when the sample is representative of blood and is inactive when the sample is representative of tissue. The use of the majority vote circuit to improve accuracy of a tissue/blood indication is described in detail in U.S. Pat. No. 5,195,521 to Melton, Jr. et al., assigned to the same assignee as this application. The disclosure of U.S. Pat. No. 5,195,521 is incorporated herein by reference.

Each active/inactive output from majority vote circuit 40 is applied to a blood/tissue accumulator $42_1$–$42_n$ where n represents the number of digitized samples along a scan line. Thus, each blood/tissue accumulator is updated each scan to enable an indication as to whether the digitized sample value represents blood or tissue. The active/inactive outputs from the majority vote circuit 40 are distributed amongst accumulators $40_1$–$42_n$ by a multiplexer arrangement (not shown).

The outputs from accumulators $42_1$–$42_n$ are applied via lines 44 to scan converter 12 (see FIG. 1). As indicated above, scan converter 12 receives a scan signal from scanner 10, which scanner signal is in the form of "fan-type" or "θ space" presentation. Thus, each scan line is defined by an angle θ. Regions along a scan line are indicative of a depth of penetration of the ultrasound signal.

Within scan converter 12, the θ-space input is converted to an X/Y space pixel representation, which representation is then stored in frame store 13 for subsequent display. Each digitized sample value from accumulators $42_1$–$42_n$ is similarly converted to a blood/tissue value representative of a pixel in X/Y space—using the same conversion process that is employed to convert the θ-space scan values to individual pixel values. Thus, each X/Y pixel stored in frame store 13 includes a further associated value which indicates its blood/tissue state.

An additional classification is performed which indicates, for each frame, at what time during the cardiac cycle, the frame displays. To enable such classification, a digitized ECG input 46 is applied to system controller 22 (FIG. 1). ECG input 46 is analyzed by system controller 22 to enable a determination to be made as to when a value thereof reaches a level indicative of the peak of the R wave. As is known to those skilled in the art, the normal ECG waveform indicates a QRS wave shape, with the R wave being indicative of onset of the systolic cycle. Thus, when system controller 22 determines a maximum value input on line 46, commencement of the systolic cycle is denoted by designating the next display frame from scan converter 12 as frame zero.

Because the peak of the R wave occurs just prior to actual mechanical contraction of the left ventricle, the frame zero image represents the onset of the actual mechanical ventricular contraction. The frame zero input to scan converter 12 also enables a triggering of the pixel classification procedure of the invention which enables the pixels to be assigned colors in accordance with their blood/tissue state and whether a frame is occurring during ventricular contraction or expansion.

Figure 3:
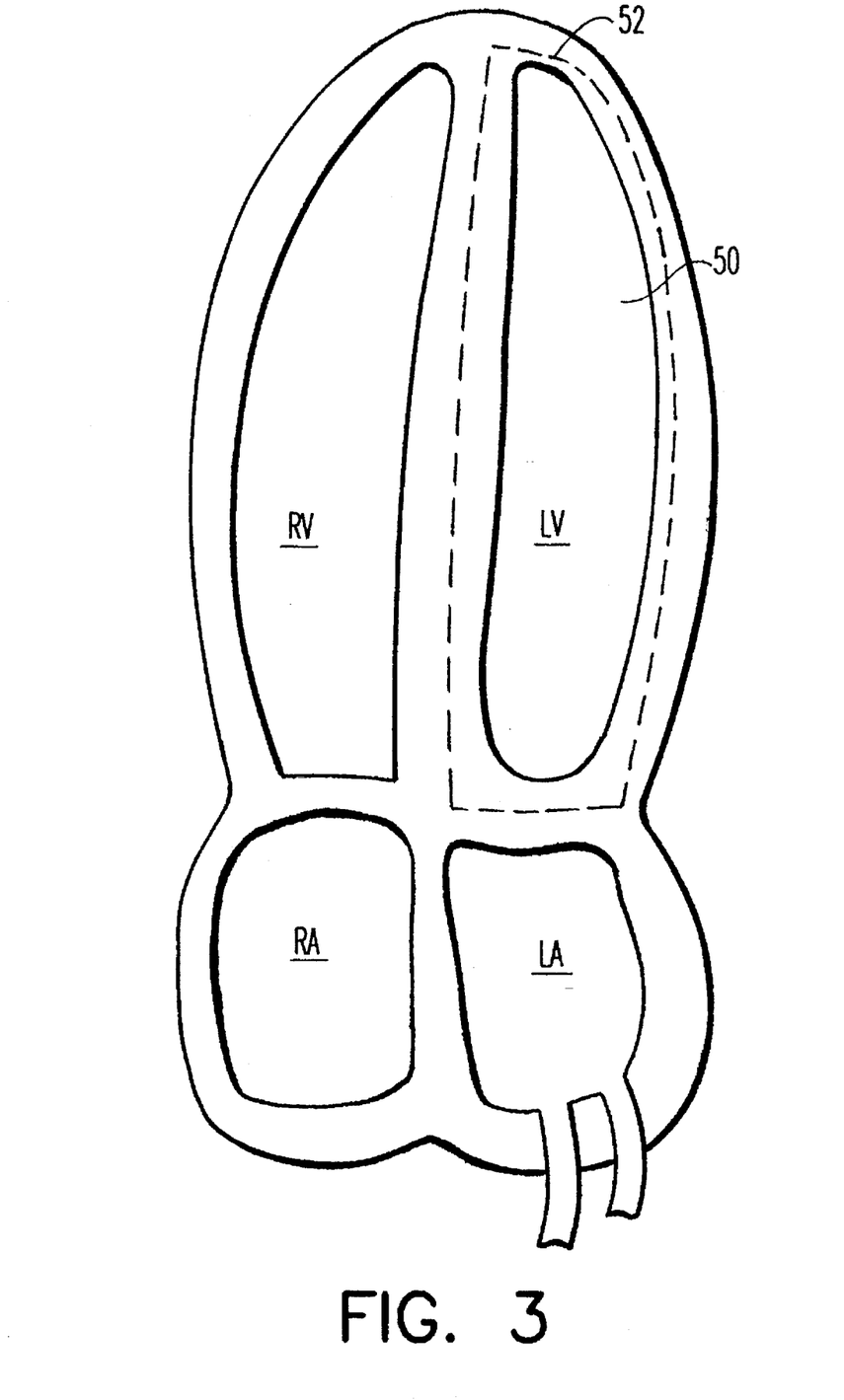
FIG. 3 is a cross-sectional view of a heart showing the left ventricle in its fully expanded state.

In FIG. 3 a simplified sectional view of a heart is shown with left ventricle 50 indicated by a region of interest outline 52 in the manner shown in U.S. Pat. No. 5,322,067. Left ventricle 50 is shown at the end of the systolic period when the left ventricular volume is at its maximum expansion.

Figure 4:
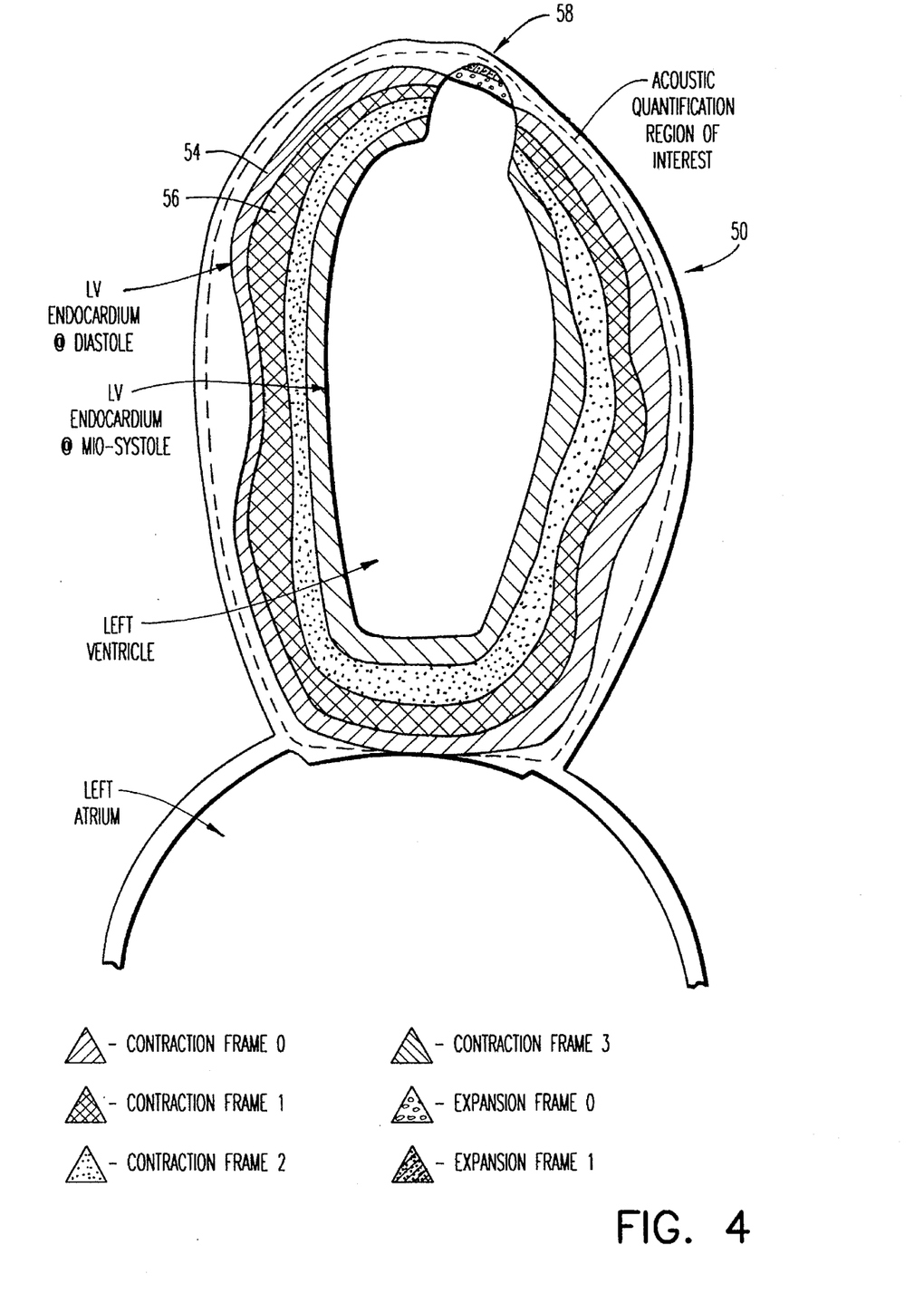
FIG. 4 is an ultrasound view of the left ventricle, over a plurality of frames, which indicates succeeding levels of contraction and expansion of the ventricular wall.

In FIG. 4, a view of left ventricle 50 is illustrated in accordance with the preferred manner it is shown by this invention. At the bottom of FIG. 4 is a legend which illustrates colors assigned to incremental endocardium changes from frame-to-frame. As indicated above, frame zero is assigned to the first ultrasound scan acquired after the peak of the R wave. In a current frame, all pixels which fall within the area between a displayed endocardium and the position of the endocardium in the preceding frame are assigned a single color—thereby enabling the incremental movement of the endocardium from one frame to the next to be viewed. Thus, in frame one, area 54 is assigned a first color to exhibit the change in endocardium position from frame zero to frame one. Similarly, in frame two, area 56 is assigned a different color to indicate endocardium movement from frame one to frame two. For each frame thereafter, a still different color is assigned to enable incremental movements of the endocardium to be visualized by the physician. Area 58 indicates an expansion of a portion of the ventricle wall that is an abnormal occurrence during a contraction cycle. However, the invention colors the pixels that transition from tissue-to-blood differently, thus enabling the physician, in a single frame, to quickly see the abnormality.

At the termination of the contraction cycle and the beginning of the expansion cycle, another series of colors is assigned to illustrate incremental differences in position between the endocardium in succeeding frames. While the preferred embodiment involves the use of series of colors to indicate incremented tissue/blood boundary changes, other mapping functions may be employed, e.g. different gray levels, different patterns, etc.

Turning now to FIGS. 5–8, the procedure employed by the system of FIG. 1 to accomplish the incremental endocardium display shown in FIG. 4 will be explained. As indicated above, for each acoustic θ-space scan, acoustic quantification unit 30 determines which acoustic samples are from tissue and which are from blood. Those indications are provided to scan converter 12.

After scan conversion from θ-space to X/Y space, a color persistence procedure is invoked which permits a combining of pixel colors from a current frame with pixel colors from an immediately preceding frame. The "combining" action operates in conjunction with a signal classification procedure to produce a color display of incremental endocardium movement. At frame zero, the persistence procedure causes tissue pixels to be marked as signal S1 and for blood pixels to be marked as signal S2. For the image frames which occur after frame zero, until the frame that is coincident with the end of the systolic period, tissue pixels are marked as signal S3 and blood pixels are marked as signal S4. For all frames after the end of the systole, all samples, both tissue and blood, are marked as signal S5.

Signals S1 and S2 set the state of all pixels, as either blood or tissue, at frame zero (start of endocardium contractile motion). For each successive frame until the end of systole, the state of each pixel for that frame is evaluated and compared to the state of the same pixel in the immediately preceding frame. The first frame in which a pixel changes from tissue-to-blood or from blood-to-tissue, such transition is noted and the pixel is color coded. The color used is dependent upon two factors. First, transitions from tissue-to-blood are given different colors than pixels which transition from blood-to-tissue. Second, pixel transitions which occur in different frames are given different colors. In this manner, it is possible to determine, from the colors of the image, both when a transition occurs and what type of transition it was.

At the end of systole, it is preferred (but not required) that acoustic quantification unit 30 outputs signal S5 for all pixels. When the color persistence function detects signal S5, all color display is suppressed. This allows the color display of endocardium motion to be limited to the systolic phase. In addition, the motion of the mitral valve is not included in the display since it is closed during the entire systolic period.

Figure 5:
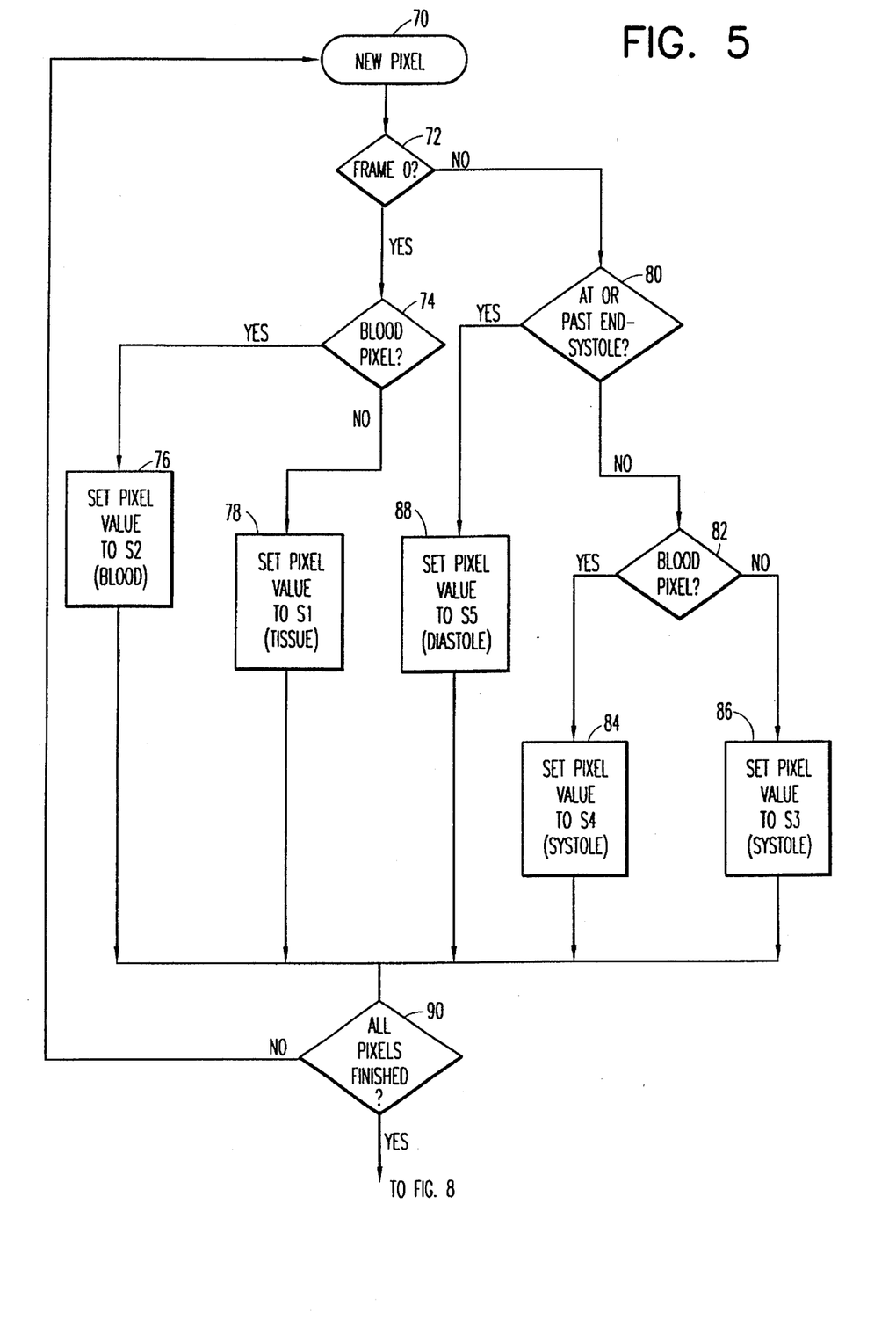
FIG. 5 is a high level logic flow diagram illustrating the procedure followed by the invention to classify image pixels as to time of occurrence during a single systole/diastole heart cycle.

Turning now to FIG. 5, the flow diagram illustrating the above noted procedure will be described. As indicated, each pixel is subjected to endocardial displacement analysis. Thus, is shown in box 70, a new acoustic pixel is received and it is determined if frame zero is being processed (decision box 72). If yes, it is determined whether acoustic quantification unit 30 has characterized the acoustic sample that corresponds to the pixel as blood or tissue (decision box 74). If the pixel is classified as blood, the pixel is assigned signal S2 (box 76). If the pixel has been classified as tissue, the pixel is assigned signal S1 (box 78).

If it is determined (in decision box 72) that frame zero is not being processed, then it is determined whether the procedure is at or past end systole (decision box 80). This is determined by noting whether a time period has transpired since the R-wave indication which exceeds a threshold value, which threshold value is in accordance with a determined systole time for the patient. If the time period has not expired, a no issues from decision box 80 and it is again determined whether the pixel is either blood or tissue (decision box 82). If the pixel is classified as blood, the pixel is assigned signal S4 (box 84) which indicates that it is a blood pixel occurring during systole. By contrast, if decision box 82 determines that the acoustic sample is tissue, the pixel is assigned signal S3, as a tissue sample occurring during systole (box 86).

Returning to decision box 80, if it is determined that the time threshold has been exceeded (i.e., that heart action is either at or past end systole), all acoustic samples, blood or tissue, are assigned signal S5 (box 88) indicating that their time of occurrence is during diastole.

It is then determined whether all acoustic samples for a given frame have been processed and, if not, the procedure cycles back to box 70 and repeats (decision box 90).

Figure 6:
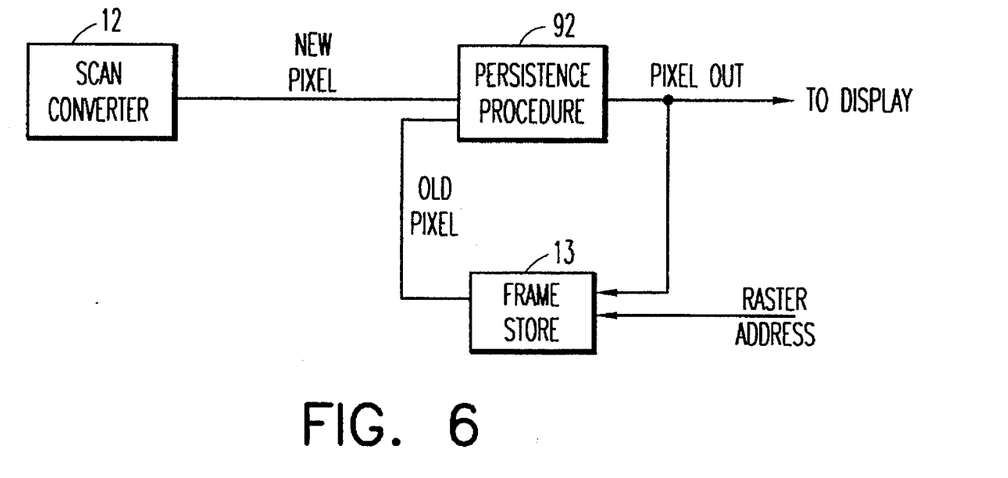
FIG. 6 is a high level block diagram illustrating inputs to a persistence procedure performed by the system of FIG. 1.

Otherwise, as shown in FIG. 6, each new pixel is subjected to a persistence procedure 92 which operates in conjunction with frame store 13 and system controller 22 to enable creation of the multicolor endocardial wall display described above. Persistence procedure 92 enables comparison of pixels occurring precisely at the same spatial location in immediately succeeding frames. The operation of persistence procedure 92 is illustrated in FIGS. 7 and 8.

Figure 7:
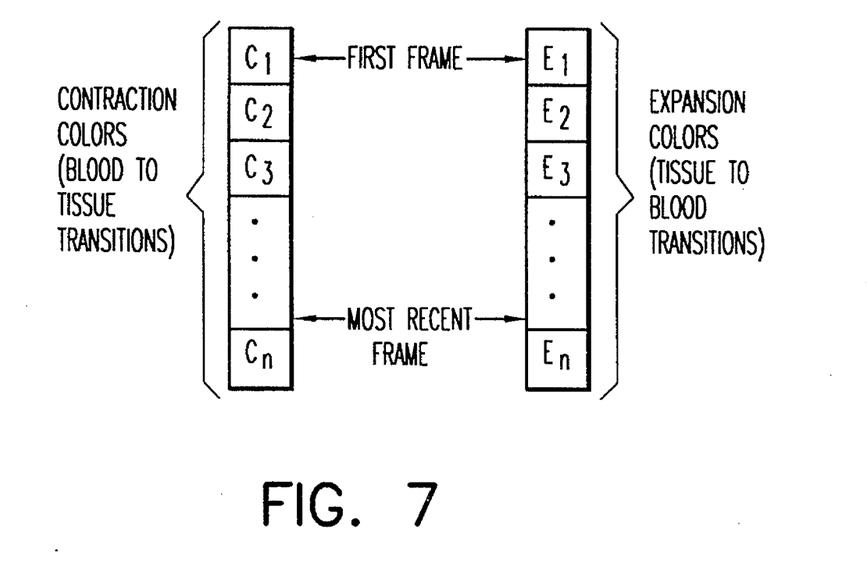
FIG. 7 illustrates the various colors assigned to pixels during both contraction and expansion cycles.
Figure 8:
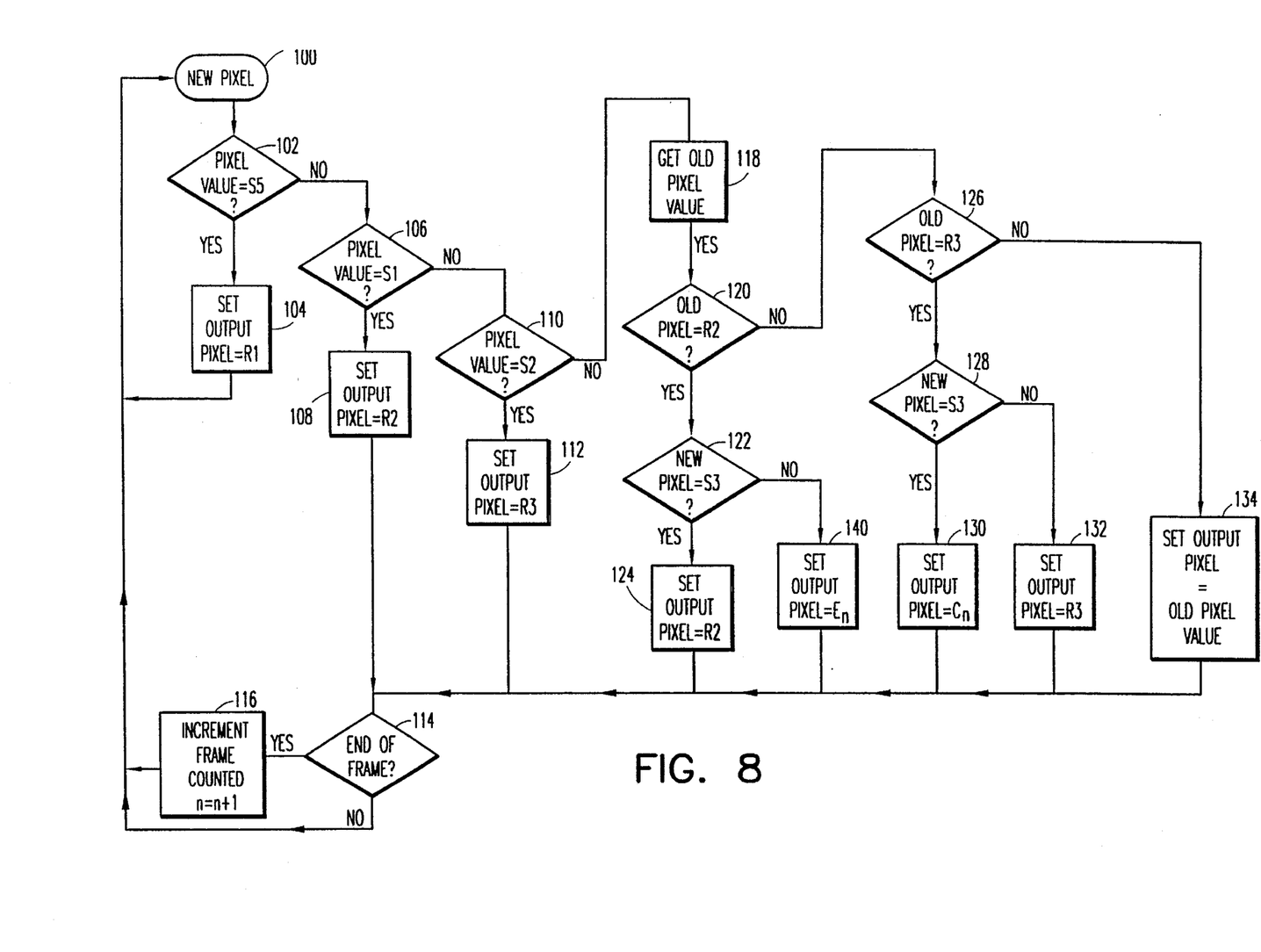
FIG. 8 is a high level flow diagram of the persistence procedure which determines a color to be assigned to each pixel in each frame of the display.

Pixel encoding symbols employed in FIGS. 7 and 8 are as follows:
S1—tissue sample pixel in frame zero
S2—blood sample pixel in frame zero
S3—tissue sample pixel from a frame between frame zero and end-systole.
S4—blood sample pixel from a frame between frame zero and end-systole
S5—tissue or blood sample pixel from frame occurring at or after end-systole and before frame zero
R1—reference color 1 (blank)
R2—reference color 2 (blank): used to designate tissue pixels
R3—reference color 3 (blank): used to designate blood pixels
$C_n$—contraction color assigned to frame n
$E_n$—expansion color assigned to frame n
n—frame number after R-wave indication (end diastole)

Referring first to FIG. 7, a chart is shown which indicates the sequence of colors $C_1$–$C_n$ which are assigned during a contraction phase of the left ventricle and enable a visualization of endocardium position changes from frame-to-frame. More specifically, each pixel which transitions from blood to tissue (during a contraction cycle) from one frame to the next is assigned a color $C_n$—thereby enabling all pixels in the frame which have transitioned from blood-to-tissue from the preceding frame to be colored $C_n$. In a similar manner, during the expansion cycle, expansion colors, $E_1$–$E_n$ are assigned to succeeding frames and denate pixels which have transitioned from tissue-to-blood, on a frame-to-frame basis.

Turning to FIG. 8, the procedure employed to enable the assignment of colors $C_1$–$C_n$ and $E_1$–$E_n$ will be described. When a new pixel is received (box 100), it is first determined whether the pixel value is S5 (decision box 102). If yes, the output pixel value is set to R1 (blank) and the procedure recycles to the next pixel (box 104). If the accessed pixel is not S5 (decision box 102), the procedure moves to decision box 106 where it is determined if the pixel value is S1 (a tissue pixel from frame zero). If yes, the output pixel value is set to R2 (box 108), designating that the pixel is a tissue pixel.

If the pixel value is not S1 (decision box 106), it is next determined whether the pixel value is equal to S2 (blood sample pixel from frame zero) (decision box 110). If yes, the output pixel value is set to R3 (box 112) designating a blood pixel. At this point, it is determined (decision box 114) as whether a last pixel has been reached (of frame zero) and if no, the procedure cycles back to box 100. If yes, the frame counter is incremented by one (box 116), and the procedure recycles to acquire the first pixel of a next frame. It is now known that the R-wave indicator has occurred, that all pixels in frame zero have been classified as either blood or tissue, and that no colors have been assigned as yet.

Turning to decision box 110, if it is determined that the pixel value is not S2 (indicating that it is either S3 or S4), the corresponding old pixel value is accessed (box 118). It is then determined whether the old pixel value is equal to R2 (a tissue pixel) (decision box 120). If yes, it is next determined whether the new pixel value is equal to S3 (a tissue sample occurring between the R-wave indicator and end systole) (decision box 122). If yes, the output pixel value is set equal to the old pixel value as there has been no change in its character and the systolic period is still in effect (box 124). Then, if not at the end of a frame (decision box 114), the procedure goes to next pixel (box 100).

Returning to decision box 120, if it is determined that the old pixel value is not R2 and it is further determined in decision box 126 that the old pixel value is R3 (a blood pixel), the procedure moves to decision box 128 where it is determined whether the new pixel value is set to S3 (indicating that it is a tissue pixel occurring in a frame between the R-wave indication and end systole) (decision box 128). If yes, the output pixel value is set to $C_n$, where n is dependent upon the frame number (box 130). It will be recalled that $C_1$–$C_n$ designate different colors that are assigned during a contraction cycle.

If decision box 128 indicates no, the output pixel value is set to R3, indicating that there has been no change from the old pixel value in the previous frame and the output pixel being considered (box 132). The procedure then recycles as shown in boxes 114, 116.

Returning to decision box 126, if it determined that the old pixel value is not equal to R3, then the output pixel value is set equal to the old pixel value (box 134) and the procedure recycles.

Returning to decision box 122, if it is determined that a new pixel value is not equal to S3, the following is known: the pixel is displayed in a frame occurring between the R-wave indication and end systole; and the pixel has changed from a tissue pixel to a blood pixel indicating an expansion of the endocardium. Thus, it is concluded that an expansion cycle has occurred. The output pixel value is set to a color value $E_n$, where n depends upon the frame number (box 140). It will be recalled that $E_1$–$E_n$ designate different colors that are assigned during an expansion cycle. The procedure then recycles through boxes 114 and box 116.

It should be understood that the foregoing description is only illustrative of the invention. Various alternatives and modifications can be devised by those skilled in the art without departing from the invention. For instance, while the invention has been described in the context of left ventricle visualization, it may be applied to any fluid-containing body cavity. Further, while a preferred method has been described for identifying pixels where a fluid/tissue boundary occurs, other boundary-determining methods known to those skilled in the art are also contemplated as within the bounds of the invention. Accordingly, the present invention is intended to embrace all such alternatives, modifications and variances which fall within the scope of the appended claims.

What is claimed is:

1. An ultrasound display apparatus for providing a two-dimensional display of a fluid filled cavity and surrounding wall tissue, said apparatus including means for indicating wall tissue displacement on said display screen and comprising:

frame comparison means for determining which pixels change from one type pixel to another type pixel in a pair of succeeding image frames, and including pixel classification means for classifying pixels in each image frame into one of two types, i.e., tissue or fluid, to facilitate determination of pixel changes; and mapping function assignment means for assigning to all changed classification pixels in a frame, a common mapping function which causes said changed classification pixels to be readily differentiated by a viewer of said display screen.

2. The ultrasound display apparatus as recited in claim 1, wherein said pixel classification means assigns to a pixel which transitions from one type to another type a first common mapping function and a assigns to a pixel which transitions from said another type to said one type a second common mapping function.

3. The ultrasound display apparatus as recited in claim 2, wherein said mapping function assignment means enables said first common mapping function and said second common mapping function to be changed in each image frame and over a succession of image frames, to enable pixel type changes from frame-to-frame to be viewed as a succession of different mapping functions to enable incremental changes in wall tissue position from frame-to-frame to be readily distinguished.

4. The ultrasound display apparatus as recited in claim 3, wherein each said common mapping function defines a different color value.

5. The ultrasound display apparatus as recited in claim 1, further comprising:

means for inputting a cardiac R-wave indication to said pixel classification means, said pixel classification means classifying each pixel in a succeeding pixel image frame as either tissue or blood, said mapping function assignment means operative during a systole period to assign to pixels, which change from fluid to tissue, a different mapping function in each succeeding frame, to enable a viewing incremental tissue wall movements from frame-to-frame to be discerned.

6. The ultrasound apparatus as recited in claim 1 wherein said frame comparison means and mapping function assignment means operate in real time as ultrasound data is accumulated.

7. A method for displaying a two dimensional image of a fluid-filled cavity and surrounding wall tissue, said method comprising the steps of:

classifying pixel images in each of a series of pixel image frames into two types, i.e., tissue or fluid;

determining which pixels change classification from one type to another type in a pair of succeeding pixel image frames; and assigning to all changed type pixels in a succeeding frame, a common color value which is different from a common color value assigned to said changed type pixels in a preceding frame, to thereby enable said changed type pixels in said succeeding frame to be readily distinguishable from changed type pixels in said preceding frame.

8. The method as recited in claim 7, wherein said assigning step assigns a first series of colors to changed type pixels in succeeding frames that occur during contraction of said wall tissue and a second series of colors to changed type pixels in succeeding frames during expansion of said wall tissue.

9. A method as recited in claim 7 wherein said assigning step assigns incrementally changed colors to changed type pixels in succeeding frames during a contraction phase of said wall tissue and further assigns sequentially changed colors to changed type pixels occurring in succeeding frames during a contraction cycle of said wall tissue.

10. The method as recited in claim 9 wherein said incremently changed colors assigned during said contraction phase are different from said incremently changed colors assigned during said expansion phase.

11. The method as recited in claim 10 wherein said method is applied to a representation of a left ventricle of a heart muscle during both systolic and diastolic sequences, said assigning step inhibited during a diastolic sequence to thereby suppress a color display during said diastolic sequence.

12. The method as recited in claim 7 wherein said method operates upon data received as a result of ultrasound scans and said classifying, determining and assigning steps occur in real time as said data is received to enable a real time viewing of said changed type pixels.

* * * * *